(12) United States Patent
Karayianni

(10) Patent No.: US 8,051,947 B2
(45) Date of Patent: Nov. 8, 2011

(54) ENERGY ABSORBING THERMOPLASTIC ELASTOMER

(75) Inventor: Eleni Karayianni, Geneva (CH)

(73) Assignee: E.I. du Pont de Nemours and Company, Wilmington, DE (US)

( * ) Notice: Subject to any disclaimer, the term of this patent is extended or adjusted under 35 U.S.C. 154(b) by 7 days.

(21) Appl. No.: 12/628,487

(22) Filed: Dec. 1, 2009

(65) Prior Publication Data

US 2010/0230203 A1 Sep. 16, 2010

Related U.S. Application Data

(60) Provisional application No. 61/210,053, filed on Mar. 12, 2009.

(51) Int. Cl.
- C08F 242/00 (2006.01)
- C08K 5/53 (2006.01)
- C09B 67/00 (2006.01)
- D02G 3/00 (2006.01)
- E04B 1/82 (2006.01)
- F16F 7/00 (2006.01)

(52) U.S. Cl. ........ 181/207; 181/290; 428/375; 524/123; 524/133; 524/502; 525/190

(58) Field of Classification Search .................. 181/207, 181/290; 524/502, 133, 123; 525/190; 428/375
See application file for complete search history.

(56) References Cited

U.S. PATENT DOCUMENTS

| | | | |
|---|---|---|---|
| 684,984 A | 10/1901 | Graft | |
| 4,415,391 A | 11/1983 | Reid | |
| 4,727,957 A | 3/1988 | Fujita | |
| 4,859,523 A | 8/1989 | Endoh et al. | |
| 4,942,219 A | 7/1990 | Yatsuka et al. | |
| 4,996,264 A | 2/1991 | Aonuma et al. | |
| 5,670,006 A * | 9/1997 | Wilfong et al. | 156/236 |
| 5,814,696 A * | 9/1998 | Saiki et al. | 524/412 |
| 5,936,048 A * | 8/1999 | Oishi et al. | 525/523 |
| 6,255,371 B1 * | 7/2001 | Schlosser et al. | 524/100 |
| 6,362,287 B1 | 3/2002 | Chorvath et al. | |
| 6,569,985 B2 | 5/2003 | McCloskey et al. | |
| 6,774,162 B1 | 8/2004 | Vortkort et al. | |
| 7,074,857 B2 * | 7/2006 | Bendler et al. | 525/176 |
| 7,425,370 B2 | 9/2008 | Nishiyama et al. | |
| 7,677,358 B2 * | 3/2010 | Tocchi et al. | 181/290 |
| 2002/0128371 A1 * | 9/2002 | Poppe et al. | 524/494 |
| 2003/0083442 A1 * | 5/2003 | Nishihara et al. | 525/464 |
| 2004/0115450 A1 * | 6/2004 | Bendler et al. | 428/480 |
| 2005/0084694 A1 * | 4/2005 | Bendler et al. | 428/480 |
| 2005/0124766 A1 | 6/2005 | Kimura | |
| 2007/0292703 A1 * | 12/2007 | Ikuta et al. | 428/494 |
| 2008/0241566 A1 | 10/2008 | Hoefflin et al. | |
| 2009/0176091 A1 * | 7/2009 | Karayianni et al. | 428/375 |
| 2009/0277716 A1 * | 11/2009 | Eadara et al. | 181/290 |
| 2010/0126796 A1 * | 5/2010 | Kadowaki | 181/207 |
| 2010/0206662 A1 * | 8/2010 | Mitsuoka et al. | 181/207 |

FOREIGN PATENT DOCUMENTS

| | | |
|---|---|---|
| EP | 1212374 | 6/2002 |
| EP | 1 921 122 | 5/2008 |
| JP | 1995216072 | 8/1995 |
| JP | 200212317 | 8/2000 |
| JP | 2000327894 | 11/2000 |
| WO | 00/75237 | 12/2000 |
| WO | 02/32998 | 4/2002 |
| WO | 2004/029155 | 4/2004 |
| WO | 2004/029155 | 8/2004 |
| WO | 2004/106052 | 12/2004 |

OTHER PUBLICATIONS

Patent Abstracts of Japan, Public No. 2002-036889, May 2, 2002, Suzuki Motor Corp.
Patent Abstracts of Japan. Publication No. 2003-278541, Feb. 10, 2003, Tokai Rubber Ind. Ltd.
Patent Abstracts of Japan, Publication No. 2007-137298, Fuji Heavy Ind. Ltd.
Patent Abstracts of Japan, Publication No. 2007-205699, Matsushita Electric Ind. Co. Ltd.
International Search Report and Written Opinion of corresponding International App. No. PCT/US2009/066780.
International Search Report and Written Opinion of related, International App. No. PCT/US2009/066676.

* cited by examiner

Primary Examiner — Elvin G Enad
Assistant Examiner — Christina Russell

(57) ABSTRACT

The present invention relates to a method for vibration damping and noise reduction by using thermoplastic vulcanizate compositions and to multilayer structures for use in vibration damping and noise reduction applications comprising at least one polymeric layer made of a thermoplastic vulcanizate composition.

15 Claims, No Drawings

ENERGY ABSORBING THERMOPLASTIC ELASTOMER

FIELD OF INVENTION

The present invention provides a method for vibration damping and noise reduction by using thermoplastic vulcanizate compositions.

BACKGROUND OF THE INVENTION

Recently, vibration and noise control have become important parameters to improve since they are related to the comfort of everyone, either in private or working spaces for example, in motor vehicles. A variety of experimental techniques exists to determine damping. The quantification of the vibration damping of a material may typically be expressed by a numerical value called tangent delta (also called tan delta, tan δ, loss tangent or loss factor) which is defined as the ratio of the loss modulus (which relates to the material's viscous behavior and defines the energy dissipation ability of the material) to the storage modulus of the material (which relates to the elastic behavior of the material and defines the energy storage ability of the material). Tan δ may be measured according to a dynamic mechanical analysis test that measures the complex modulus of the material as a measure of the dissipation of external vibrational energy. Typical viscoelastic materials present a strong dependence over the temperature and frequency range in which they are used as demonstrated by the presence of different state regions in distinct temperature or frequency regions: the Glassy, the Transition, the Rubbery and the Flow Regions. The material presents the highest storage modulus and therefore very low damping level at the Glassy Region, while it shows the most rapid change in storage modulus in the Transition Region from the glassy to the rubbery state and thus it is in this region that the material possesses its highest level of damping performance. Tan δ typically shows a maximum peak in this region which also can be used to define the glass transition temperature of the material. In the rubbery state both the storage modulus and the loss factor obtain somewhat low values and vary more slowly with changes in temperature and frequency. In the Flow region where the material continues to soften with increasing temperature the loss factor can attain very high values. The variation of the storage modulus and loss factor of a typical viscoelastic material with frequency shows that the effect of increasing temperature on the storage modulus is similar to the effect of reducing frequency thus governed by a temperature-frequency super-position principle which can be used to transform the material properties from the temperature domain to the frequency domain and vice-versa. The greater the value of tan δ, the better the vibration and noise reduction.

Absorption into the material reduces the vibrational energy transmitted, for example, to a passenger, and the noise that comes. Materials which exhibit efficient vibration damping show a high conversion of vibrational energy into other forms of energy, such as heat, i.e. they have a high tan δ. Such materials have a wide range of applications where vibration and noise is of concern, such as for example as components of motor vehicles, commercial airplanes, aerospace, household appliances, computer hardware, recreation and sports, machines, power equipment, buildings or mechanical devices.

For many applications, efficient vibration damping is desired over a broad range of temperature. In the automotive industry for example, materials used to dampen noises and vibrations should have sufficient tan δ values in a temperature range lying from about −35 to 80° C.

Various vibration damping and noise reduction materials have been described in the literature. JP 2000327894 discloses unsaturated polyester resins constituent for vibration damping. The unsaturated polyester resin composition comprises unsaturated polyester, ethylenically unsaturated monomer and graft copolymer. The graft copolymer consists of segment (A) comprising a thermoplastic elastomer and segment (B) comprising (co)polymer of (meth)acrylate. The disclosed resins have tan δ values equal or superior to 0.014 at 25 and 30° C.

U.S. Pat. No. 4,859,523 discloses vibration damping polyurethane resins produced by the reaction of an aromatic polyester diol, an aliphatic polyester diol, a diisocyanate compound and a chain extender. Such resins are useful for providing a composite vibration damping steel plate comprising two metal plate layers and the layer of the viscoelastic resin sandwiched between the metal layers. Such resins are reported to have glass transition temperature and therefore expected maximum tan δ value at various temperatures between 0° C. to 70° C. Such resins are reported to have a vibration damping peak temperature between 60° C. and 120° C. as determined by sandwiching the resin between two steel plates at a frequency of vibration of 500 Hz.

U.S. Pat. No. 5,356,715 discloses linear, high molecular weight polymers having blocks of epoxy and polyester or polyether resins said to be useful for forming vibration damping composites in metal sandwich structures.

WO 2004/106052 discloses housings said to be suitable for the attenuation of sound. Such housings comprise a plurality of rigid polymer layers separated by flexible polymer layers, wherein the flexible polymer layer is made of a thermoplastic elastomer having a polybutylene terephthalate hard segment and a glycol soft segment.

JP 2000212317 discloses a foamed polyester sheet comprising a copolyester and JP 07216072 discloses polyether ester block copolymers said to show low-temperature high vibration damping performance. JP 061361064 discloses sheets for sound deadening consisting of thermoplastic copolymerized polyester. U.S. Pat. No. 4,942,219 discloses the use of an amorphous block copolyester resin for a composite vibration damping material. US 5814696 discloses a polyester resin comprising an aromatic polyester resin and a polyester block copolymer resin.

EP 1212374 discloses sound damping polyester compositions comprising isoprenoid rubber modifier and a polyester selected from the group of consisting of poly(ethylene terephthalate) (PET), poly(propylene terephthalate) (PPT), poly(butylene terephthalate) (PBT), poly(ethylene naphthanoate) (PEN), poly(butylene naphthanoate) (PBN) and mixtures thereof. U.S. Pat. No. 6,849,684 and WO 2002/032998 disclose a molded composition of a noise damping material made of a blend of a soft thermoplastic polyether and a hard polyester resin reinforced with a fibrous or particulate filler.

A need remains for materials having good vibration dampening and noise reduction performance over extendable temperature range (e.g. from −35 and 80° C.).

SUMMARY OF THE INVENTION

The inventors have surprisingly found that melt-processable thermoplastic vulcanizate compositions have an excellent vibration damping and noise reduction behavior over a range of temperature and frequency.

Described herein are methods of using a thermoplastic vulcanizate composition for vibration damping and noise reduction applications, comprising:

a) making a thermoplastic vulcanizate composition comprising:
  (i) from about 15 to about 75 wt-% of at least one thermoplastic polyester or copolyetherester elastomer continuous phase; and
  (ii) from about 25 to about 85 wt-% of at least one poly(meth)acrylate or polyethylene/(meth)acrylate rubber that forms a dispersed phase, wherein the rubber is dynamically cross-linked with at least one peroxide free-radical initiator and at least one organic multiolefinic co-agent; the weight percentage being based on the total weight of the thermoplastic vulcanizate composition (i+ii); and
b) making an article comprising the thermoplastic composition of (a);
c) optionally shaping the article of (b) so as to dampen vibration; and
d) applying the article of (b) or (c) to an appliance.

Also described herein are methods of improving vibration damping and noise reduction in a wide range of temperature and frequency by a) making a thermoplastic vulcanizate composition comprising:
  (i) from about 15 to about 75 wt-% of at least one thermoplastic polyester or copolyetherester elastomer continuous phase; and
  (ii) from about 25 to about 85 wt-% of at least one poly(meth)acrylate or polyethylene/(meth)acrylate rubber that forms a dispersed phase, wherein the rubber is dynamically cross-linked with at least one peroxide free-radical initiator and at least one organic multiolefinic co-agent;
  the weight percentage being based on the total weight of the thermoplastic vulcanizate composition (i+ii); and
b) making an article comprising the thermoplastic composition of (a);
c) optionally shaping the article of (b) so as to dampen vibration; and
d) applying the article of (b) or (c) to an appliance.

Also described herein are methods of making an article comprising:
shaping the above described thermoplastic vulcanizate, wherein said article demonstrates efficient vibration damping and noise reduction characteristics over a temperature range lying from at or about −35° C. to at or about 80° C.

Also described herein are multilayer structures for use in vibration damping and noise reduction applications.

DETAILED DESCRIPTION OF THE INVENTION

Definitions and Abbreviations

As used herein, the terms "about" and "at or about" mean that the amount or value in question may be the value designated or some other value about the same, and convey that similar values promote equivalent results or effects according to the methods described herein.

As used herein, the term "chosen among" means "selected from the group consisting of," in that a selection is made from the recited groups.

As used herein, the term "efficient materials used to dampen noises and vibrations" refers to materials having tan δ values reaching at least values of 0.07.

As used herein, the term "appliance" refers to any device in which vibration damping and/or noise reduction is desired and can include, for example, household appliances, structural components for machines, structural components for buildings, structural components for mechanical devices, and automotive components.

As used herein, the abbreviation "wt-%" refers to "weight percent".

As used herein, the term "thermoplastic vulcanizates" or "TPVs" refer to blends consisting of a continuous thermoplastic phase with a phase of vulcanized elastomer dispersed therein. "Vulcanizate" and "vulcanizate rubber" are generic terms that refer to the cured or partially cured, cross-linked or cross-linkable rubber as well as curable precursors of cross-linked rubber and as such include elastomers, gum rubbers and so-called soft vulcanizates as commonly recognized in the art.

Efficient noise reduction is desired over a broad range of temperature and frequency. In the context of this invention, a broad temperature range means temperatures lying between −35 and 80° C. A broad frequency range means frequencies lying above 1 Hz, preferably between 1 Hz and 1600 Hz and more preferably between 100 Hz and 1000 Hz. Moreover, it is meant that this efficiency is required either for applications that are subjected to large temperature variations or for a wide range of applications at specific temperatures.

TPVs combine many desirable characteristics of cross-linked rubbers with some characteristics of thermoplastic elastomers. TPVs compositions used in the present inventions are described in U.S. Pat. No. 7,074,857, US 2005084694 and WO 2004/029155, which are hereby incorporated by reference herein. An example of TPV is disclosed in WO 2004/029155 describing a curable thermoplastic blend comprising a polyalkylene phthalate polyester polymer or copolymer and a cross-linkable poly(meth)acrylate or polyethylene/(meth)acrylate vulcanizate rubber in combination with an effective amount of peroxide free-radical initiator and an organic multiolefinic co-agent to cross-link the rubber during extrusion or injection moulding of the vulcanizate thermoplastic elastomeric blend. As used herein, the term "organic multiolefinic co-agent" is intended to mean organic co-agents that contain two or more unsaturated double bonds. When the vulcanizate blend is melt extruded, the result is a TPV that can be processed in many ways like a thermoplastic, but which has the characteristics of a cross-linked rubber. In contrast to conventional vulcanizates thermosets, TPVs can be injection-molded, or extruded without requiring further curing.

Described herein are thermoplastic vulcanizates for use in vibration damping and noise reduction applications, which comprise (i) from at or about 15 to at or about 75 wt-%, or preferably from at or about 15 to at or about 60 wt-%, of at least one thermoplastic polyester that forms a continuous phase; and (ii) from at or about 25 to at or about 85 wt-%, or preferably from at or about 40 to at or about 85 wt-% of at least one poly(meth)acrylate or polyethylene/(meth)acrylate rubber that forms a dispersed phase, wherein the rubber is dynamically cross-linked with at least one peroxide free radical initiator and at least one organic multiolefinic co-agent, the weight percentage of components (i) and (ii) being based on the total weight of (i)+(ii). Such thermoplastic vulcanizates are described in WO 2004/029155.

As used herein, the term "(meth)acrylic acid" refers to methacrylic acid and/or acrylic acid; the term "(meth)acrylate" refers to methacrylate and/or acrylate and the term "poly(meth)acrylate refers to polymers derived from the polymerization of methacrylate and/or acrylate monomers. As used herein, the term "thermoplastic polyester" refers to component (i) and includes thermoplastic polyester elastomers. As used herein, the term "acrylate rubber" refers to poly(meth) acrylate or polyethylene/(meth)acrylate rubber.

The acrylate rubber may be prepared by copolymerizing one or more (meth)acrylate monomers with one or more olefins. A preferred olefin is ethylene. As used herein, the term "cross-linked acrylate rubber" refers to component (ii). Preferably, the acrylate rubber includes poly(alkyl (meth) acrylate) rubbers, ethylene/alkyl (meth)acrylate copolymer rubber and poly(perfluoroalkyl (meth)acrylate) rubber, and are more preferably an ethylene/alkyl (meth)acrylate copolymer rubbers where the alkyl group has from 1 to 4 carbons. Preferred ethylene/alkyl (meth)acrylate copolymers are those derived from less than about 80 wt-% of ethylene and more than about 20 wt-% alkyl (meth)acrylate.

The acrylate rubbers may optionally comprise additional repeat units derived from one or more functionalized comonomers, such as (meth)acrylate glycidyl esters (such as glycidyl methacrylate), maleic acid, or other comonomer having one or more reactive groups including acid, hydroxyl, epoxy, isocyanates, amine, oxazoline, chloroacetate, or diene functionality.

The acrylate rubbers may also be made from more than two (meth)acrylate monomers. Examples are acrylate rubbers made by polymerizing ethylene, methyl acrylate, and a second acrylate (such as butyl acrylate).

Preferred thermoplastic polyesters are typically derived from one or more dicarboxylic acids (where herein the term "dicarboxylic acid" also refers to dicarboxylic acid derivatives such as esters) and one or more diols. In preferred polyesters the dicarboxylic acids comprise one or more of terephthalic acid, isophthalic acid, and 2,6-naphthalene dicarboxylic acid, and the diol component comprises one or more of HO(CH$_2$)$_n$OH (I); 1,4-cyclohexanedimethanol; HO(CH$_2$CH$_2$O)$_m$CH$_2$CH$_2$OH (II); and HO(CH$_2$CH$_2$CH$_2$CH$_2$O)$_z$CH$_2$CH$_2$CH$_2$CH$_2$OH (III), wherein n is an integer of 2 to 10, m on average is 1 to 4, and z is on average about 7 to about 40. Note that (II) and (III) may be a mixture of compounds in which m and z, respectively, may vary and that since m and z are averages, they do not have to be integers. Other dicarboxylic acids that may be used to form the thermoplastic polyester include sebacic and adipic acids. Hydroxycarboxylic acids such as hydroxybenzoic acid may be used as comonomers. Specific preferred polyesters include poly(ethylene terephthalate) (PET), poly(trimethylene terephthalate) (PTT), poly(1,4-butylene terephthalate) (PBT), poly(ethylene 2,6-naphthoate), and poly(1,4-cyclohexyldimethylene terephthalate) (PCT).

The thermoplastic polyester may be a thermoplastic polyester elastomer, such as a copolyetherester. Useful copolyetheresters are copolymers that have a multiplicity of recurring long-chain ester units and short-chain ester units joined head-to-tail through ester linkages, said long-chain ester units being represented by formula (A):

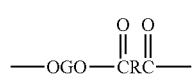

(A)

and said short-chain ester units being represented by formula (B):

(B)

wherein:

G is a divalent radical remaining after the removal of terminal hydroxyl groups from poly(alkylene oxide)glycols having a number average molecular weight of between about 400 and about 6000, or preferably between about 400 and about 3000;

R is a divalent radical remaining after removal of carboxyl groups from a dicarboxylic acid having a molecular weight of less than about 300;

D is a divalent radical remaining after removal of hydroxyl groups from a diol having a molecular weight less than about 250.

As used herein, the term "long-chain ester units" as applied to units in a polymer chain refers to the reaction product of a long-chain glycol with a dicarboxylic acid. Suitable long-chain glycols are poly(alkylene oxide) glycols having terminal (or as nearly terminal as possible) hydroxy groups and having a number average molecular weight of from about 400 to about 6000, and preferably from about 600 to about 3000. Preferred poly(alkylene oxide) glycols include poly(tetramethylene oxide) glycol, poly(trimethylene oxide) glycol, poly(propylene oxide) glycol, poly(ethylene oxide) glycol, copolymer glycols of these alkylene oxides, and block copolymers such as ethylene oxide-capped poly(propylene oxide) glycol. Mixtures of two or more of these glycols can be used.

As used herein, the term "short-chain ester units" as applied to units in a polymer chain of the copolyetheresters refers to low molecular weight compounds or polymer chain units having molecular weights less than about 550. They are made by reacting a low molecular weight diol or a mixture of diols (molecular weight below about 250) with a dicarboxylic acid to form ester units represented by Formula (B) above.

Included among the low molecular weight diols which react to form short-chain ester units suitable for use for preparing copolyetheresters are acyclic, alicyclic and aromatic dihydroxy compounds. Preferred compounds are diols with about 2-15 carbon atoms such as ethylene, propylene, isobutylene, tetramethylene, 1,4-pentamethylene, 2,2-dimethyltrimethylene, hexamethylene and decamethylene glycols, dihydroxycyclohexane, cyclohexane dimethanol, resorcinol, hydroquinone, 1,5-dihydroxynaphthalene, etc. Especially preferred diols are aliphatic diols containing 2-8 carbon atoms, and a more preferred diol is 1,4-butanediol. Included among the bisphenols which can be used are bis(p-hydroxy) diphenyl, bis(p-hydroxyphenyl)methane, and bis(p-hydroxyphenyl)propane. Equivalent ester-forming derivatives of diols are also useful (e.g., ethylene oxide or ethylene carbonate can be used in place of ethylene glycol or resorcinol diacetate can be used in place of resorcinol). As used herein, the term "diols" includes equivalent ester-forming derivatives such as those mentioned. However, any molecular weight requirements refer to the corresponding diols, not their derivatives.

Dicarboxylic acids that can react with the foregoing long-chain glycols and low molecular weight diols to produce the copolyetheresters are aliphatic, cycloaliphatic or aromatic dicarboxylic acids of a low molecular weight, i.e. having a molecular weight of less than about 300. The term "dicarboxylic acids" as used herein includes functional equivalents of dicarboxylic acids that have two carboxyl functional groups that perform substantially like dicarboxylic acids in reaction with glycols and diols in forming copolyetherester polymers. These equivalents include esters and ester-forming derivatives such as acid halides and anhydrides. The molecular weight requirement pertains to the acid and not to its equivalent ester or ester-forming derivative. Thus, an ester of a dicarboxylic acid having a molecular weight greater than 300 or a functional equivalent of a dicarboxylic acid having a molecular weight greater than 300 are included provided the corresponding acid has a molecular weight below about 300. The dicarboxylic acids can contain any substituent groups or combinations that do not substantially interfere with the copolyetherester polymer formation and use of the polymer in the compositions of this invention.

The term "aliphatic dicarboxylic acids," as used herein, refers to carboxylic acids having two carboxyl groups each attached to a saturated carbon atom. If the carbon atom to which the carboxyl group is attached is saturated and is in a ring, the acid is cycloaliphatic. Aliphatic or cycloaliphatic acids having conjugated unsaturation often cannot be used because of homopolymerization. However, some unsaturated acids, such as maleic acid, can be used.

Aromatic dicarboxylic acids, as the term is used herein, are dicarboxylic acids having two carboxyl groups each attached to a carbon atom in a carbocyclic aromatic ring structure. It is not necessary that both functional carboxyl groups be attached to the same aromatic ring and where more than one ring is present, they can be joined by aliphatic or aromatic divalent radicals or divalent radicals such as —O— or —SO$_2$—.

Representative useful aliphatic and cycloaliphatic acids that can be used include sebacic acid; 1,3-cyclohexane dicarboxylic acid; 1,4-cyclohexane dicarboxylic acid; adipic acid; glutaric acid; 4-cyclohexane-1,2-dicarboxylic acid; 2-ethylsuberic acid; cyclopentanedicarboxylic acid decahydro-1,5-naphthylene dicarboxylic acid; 4,4'-bicyclohexyl dicarboxylic acid; decahydro-2,6-naphthylene dicarboxylic acid; 4,4'-methylenebis(cyclohexyl) carboxylic acid; and 3,4-furan dicarboxylic acid. Preferred acids are cyclohexane-dicarboxylic acids and adipic acid.

Representative aromatic dicarboxylic acids include phthalic, terephthalic and isophthalic acids; bibenzoic acid; substituted dicarboxy compounds with two benzene nuclei such as bis(p-carboxyphenyl)methane; p-oxy-1,5-naphthalene dicarboxylic acid; 2,6naphthalene dicarboxylic acid; 2,7-naphthalene dicarboxylic acid; 4,4'-sulfonyl dibenzoic acid and $C_1$-$C_{12}$ alkyl and ring substitution derivatives thereof, such as halo, alkoxy, and aryl derivatives. Hydroxyl acids such as p-(beta-hydroxyethoxy)benzoic acid can also be used provided an aromatic dicarboxylic acid is also used.

Aromatic dicarboxylic acids are a preferred class for preparing the copolyetherester polymers useful for this invention. Among the aromatic acids, those with 8-16 carbon atoms are preferred, particularly terephthalic acid alone or with a mixture of phthalic and/or isophthalic acids.

The copolyetheresters preferably comprise at or about 15 to at or about 99 wt-% short-chain ester units corresponding to Formula (B) above, the remainder being long-chain ester units corresponding to Formula (A) above. The copolyetheresters more preferably comprise at or about 20 to at or about 95 wt-%, and even more preferably at or about 50 to at or about 90 wt-% short-chain ester units, where the remainder is long-chain ester units. More preferably, at least about 70% of the groups represented by R in Formulae (A) and (B) above are 1,4-phenylene radicals and at least about 70% of the groups represented by D in Formula (B) above are 1,4-butylene radicals and the sum of the percentages of R groups which are not 1,4-phenylene radicals and D groups that are not 1,4-butylene radicals does not exceed 30%. If a second dicarboxylic acid is used to make the copolyetherester, isophthalic acid is preferred and if a second low molecular weight diol is used, ethylene glycol, 1,3-propanediol, cyclohexanedimethanol, or hexamethylene glycol are preferred.

A blend or mixture of two or more copolyetherester elastomers can be used. The copolyetherester elastomers used in the blend need not on an individual basis come within the values disclosed hereinbefore for the elastomers. However, the blend of two or more copolyetherester elastomers must conform to the values described herein for the copolyetheresters on a weighted average basis. For example, in a mixture that contains equal amounts of two copolyetherester elastomers, one copolyetherester can contain 60 wt-% short-chain ester units and the other copolyetherester can contain 30 wt-% short-chain ester units for a weighted average of 45 wt-% short-chain ester units.

Preferably, the copolyetherester elastomers used for the present invention are prepared from monomers comprising isophthalic acid and/or terephthalic acid; poly(tetramethylene oxide) glycol, poly(trimethylene oxide) glycol or ethylene oxide-capped poly(propylene oxide) glycol; and 1,4-butanediol and/or 1,3-propanediol, or are prepared from esters of terephthalic acid, e.g. dimethylterephthalate, 1,4-butanediol and poly(ethylene oxide)glycol. More preferably, the copolyetherester elastomers are prepared from esters of terephthalic acid, e.g. dimethylterephthalate, 1,4-butanediol and poly(tetramethylene ether)glycol.

Examples of suitable copolyetherester elastomer as continuous phase of thermoplastic vulcanizates are commercially available under the trademark Hytrel® from E. I. du Pont de Nemours and Company, Wilmington, Del.

Suitable organic multiolefinic co-agents include but are not limited to diethylene glycol diacrylate; diethylene glycol dimethacrylate; N,N'-m-phenylene dimaleimide; triallylisocyanurate; trimethylolpropane trimethacrylate; tetraallyloxyethane; triallyl cyanurate; tetramethylene diacrylate; polyethylene glycol dimethacrylate; and the like.

Suitable free-radical initiators include but are not limited to 2,5-dimethyl-2,5-di-(t-butylperoxy)hexyne-3; t-butyl peroxybenzoate; 2,5-dimethyl-2,5-di-(t-butylperoxy)hexane; dicumyl peroxide; α,α-bis(t-butylperoxy)-2,5-dimethylhexane; and the like.

The thermoplastic vulcanizate used for the present invention may be prepared using processes such as those described in WO 2004/029155. The actual mixing of components and subsequent dynamic cross-linking may be performed either in a batch mode or a continuous mode using conventional melt blending equipment. An example is a process comprising the steps of:

(a) adding and admixing a cross-linkable poly(meth)acrylate or polyethylene/(meth)acrylate vulcanizate rubber, at least one peroxide free-radical initiator and at least one organic multi-olefinic co-agent in a melt extruder or melt blender at a temperature insufficient to promote significant cross-linking;

(b) adding a polyester polymer or copolymer to the melt extruder or melt blender and admixing the polyester polymer with the cross-linkable poly(meth)acrylate or polyethylene/(meth)acrylate vulcanizate rubber prior to cross-linking;

(c) further mixing the cross-linkable poly(meth)acrylate or polyethylene/(meth)acrylate vulcanizate rubber with the at least one peroxide free radical initiator and the at least one organic multiolefinic co-agent with the polyester polymer or copolymer at conditions and temperature sufficient to cross-link the cross-linkable poly(meth)acrylate or polyethylene/(meth)acrylate vulcanizate rubber; and (d) recovering the thermoplastic vulcanizate comprising the polyester polymer or copolymer as a continuous phase and of the poly(meth)acrylate or polyethylene/(meth)acrylate vulcanizate rubber cross-linked with the at least one peroxide free radical initiator and the at least one organic multiolefinic co-agent as a disperse phase.

The thermoplastic vulcanizate composition for use in vibration damping and noise reduction may further comprise one or more heat stabilizer and/or antioxidants. Examples of suitable heat stabilizers and/or antioxidants include diphenylamines, amides, thioesters, phenolic antioxidants, and phosphites. When used, the heat stabilizers and/or antioxidants are preferably present in at or about 0.01 to at or about 5 wt-%, or more preferably in at or about 0.01 to at or about 2 wt-%, the weight percent being based on the total weight of the thermoplastic vulcanizate composition.

The thermoplastic vulcanizate composition for use in vibration damping and noise reduction may further comprise additional additives such as, colorants, lubricants, fillers and reinforcing agents, flame retardants, conductive additives, viscosity modifiers, nucleating agents, plasticizers, mold release agents, scratch and mar modifiers, drip suppressants, and adhesion modifiers. When used, additional compounds are preferably present in at or about 0.1 to at or about 30 wt-%, or preferably in at or about 0.1 to at or about 20 wt-%, the weight percent being based on the total weight of the composition.

The compositions are melt-mixed blends, wherein all of the polymeric components are well-dispersed within each other and all of the non-polymeric ingredients are well-dispersed in and bound by the polymer matrix, such that the blend forms a unified whole. Any melt-mixing method may be used to combine the polymeric components and non-polymeric ingredients of the present invention. For example, the polymeric components and non-polymeric ingredients may be added to a melt mixer, such as, for example, a single or twin-screw extruder; a blender; a single or twin-screw kneader; a Haake mixer, a Brabender mixer, a Banbury mixer, or a roll mixer, either all at once through a single step addition, or in a stepwise fashion, and then melt-mixed. When adding the polymeric components and non-polymeric ingredients in a stepwise fashion, part of the polymeric components and/or non-polymeric ingredients are first added and melt-mixed with the remaining polymeric components and non-polymeric ingredients being subsequently added and further melt-mixed until a well-mixed composition is obtained.

Also described herein are methods of making an article comprising a step of shaping a thermoplastic vulcanizate composition of the invention. Examples of articles are vibration damping and noise reduction structures. By "shaping", it is meant any shaping technique, such as for example extrusion or any molding process known to one of ordinary skill in the art, comprising for example injection molding, compression molding or blow molding.

Also described herein are multilayer structures for use in vibration damping and noise reduction applications comprising at least one polymeric layer comprising the thermoplastic vulcanizate described above and at least one additional layer. The at least one polymeric layer comprising the thermoplastic vulcanizate may be used as an inner layer that is adjacent to the at least one additional layer, may be used as a middle layer comprised between additional layers leading to a multilayer structure consisting of at least two additional layers sandwiching the at least one polymeric layer comprising the thermoplastic vulcanizate, or may be used as an external layer that is adjacent to at least one additional layer. The at least one additional layer of the multilayer structure may be made from, e. g. polymers others than thermoplastic vulcanizates, adhesive layers, metals, glass, wood, fibers, fabrics, metal oxides, stone and concrete. Examples of polymers others than thermoplastic vulcanizates are thermoplastic polymers, thermoplastic elastomers, thermoplastic copolyesters or polymers exhibiting high stiffness and/or high temperature resistance.

In a preferred structure for automotive use, the multilayer structure consists of a 2-layers structure comprising one polymeric layer comprising at least one thermoplastic vulcanizate and one additional layer which is an outside layer facing the environment. This outside layer is preferably made from polymers others than thermoplastic vulcanizates, metals, glass, wood, fibers, fabrics, metal oxides, stone or concrete. Preferably, the one additional layer is made of a metal and more preferably the additional layer is made of a metal chosen among aluminum, aluminum alloys, copper, bronze, steel, stainless steel, chrome or titanium and mixtures thereof. Should the adhesion between the additional layer and the polymeric layer comprising at least one thermoplastic vulcanizate be insufficient, one or more adhesive layers can be added between the different layers. The thickness of the polymeric layer comprising at least one thermoplastic vulcanizate for use in the 2-layers structure is preferably at least about 10 µm, and more preferably between 200 and 500 µm.

In another preferred structure for automotive use, the multilayer structure consists of at least two additional layers that "sandwich" the at least one polymeric layer comprising at least one thermoplastic vulcanizate so as to form a sandwich structure, that is, the at least one polymeric layer lies between the additional layers. The thickness of the at least one polymeric layer for use in the sandwich structure is preferably at least about 10 µm, more preferably between 25 and 500 µm and still more preferably between 25 and 250 µm. Preferably, the at least two additional layers sandwiching the at least one polymeric layer are made of a metal and more preferably from a metal chosen among aluminum, aluminum alloys, copper, bronze, steel, stainless steel, chrome or titanium and mixtures thereof. These metals may also be surface treated or have thereon surface conversion coatings. The additional layers on each side of the polymeric layer can be formed of the same metal or of different metals and can have same or different thicknesses. The choice of the metal of the at least two additional layers outer layer is not critical and the above-exemplified metals are properly chosen depending on each purpose of use.

The multilayer structures described herein for use in vibration damping and noise reduction applications can further comprise a printable and/or colorable layer. The printable and/or colorable layer is preferably positioned on the outermost additional layer surface of the multilayer structure. The printable and/or colorable layer can be a polymeric film, paper, board, and combinations thereof.

These multilayer structures that comprise one or more additional layers made of metal and the thermoplastic vulcanizate can be manufactured by a single process which may include laminating or extrusion coating the thermoplastic vulcanizate material onto the metal layer. Alternatively, these multilayer structures can be manufactured by using pressure and heat to bind a polymeric layer comprising at least one thermoplastic vulcanizate and a metal layer. If one or more layers are needed between the thermoplastic vulcanizate layer and the additional layer made of metal as described above, the multilayer structure is manufactured by a single process including co-extrusion coating the layer and the polymeric material onto the metal layer. A film containing at least one layer made of the thermoplastic vulcanizate described herein can be produced via cast-film mono- or multi-layer extrusion, or blown film mono- or multi-layer extrusion processes and the surface of the film treated so as to promote adhesion to the additional layer made of metal or to increase surface smoothness.

The multilayer structures described herein may be used in applications where vibration damping and noise reduction is of concern, like for example for household appliance (washers, dryers, refrigerators, air conditioning, heating), structural component for machines (computers, disk drives), structural component for buildings or mechanical devices (fan, switches, compressor).

The multilayer structures described herein may be used in automotive applications to dampen the vibration and the noise arising from the motor, the engine, climate control systems, the road or environment inputs, the rolling noise of car tires or from any other noise emitters. Examples of vibration damping and noise reduction components of vehicles are body panels, dashboards, engine covers, rocker panels or air filters covers.

The compositions used in the methods and structures described herein have the particular advantage of having high elongation, good chemical and temperature resistance, high melting temperatures exceeding 200° C., and flexural stiffness. This unique combination of properties makes them very attractive candidates for use in composite structures in automotive applications requiring formability and paint bake oven stability.

The invention is further described in the Examples below, which illustrate but do not limit the scope of the methods and structures described herein.

EXAMPLES

The following materials were used for preparing the thermoplastic vulcanizate compositions used for the present invention and comparative examples.

Copolyetherester N° 1

Comparative Example C1

A copolyetherester elastomer containing about 35.3 wt-% of poly(tetramethylene oxide) having an average molecular weight of about 1000 g/mol as polyether block segments, the weight percentage being based on the total weight of the copolyetherester elastomer. The short chain ester units were polybutylene terephthalate segments.

Copolyetherester N° 2

Comparative Example C2

A copolyetherester elastomer containing about 15.8 wt-% of poly(tetramethylene oxide) having an average molecular weight of about 1000 g/mol as polyether block segments, the weight percentage being based on the total weight of the copolyetherester elastomer. The short chain ester units were polybutylene terephthalate segments.

Copolyetherester N° 3

Comparative Example C3

A copolyetherester elastomer containing about 44.0 wt-% of poly(propylene oxide) end-capped with about 30 wt-% of poly(ethylene oxide) units having an average molecular weight of about 2150 g/mol as polyether block segments, the weight percentage being based on the total weight of the copolyetherester elastomer. The short chain ester units were polybutylene terephthalate segments.

As required for the manufacturing process of copolyetherester and well-known to those skilled in the art, copolyetheresters N° 1, N° 2 and N° 3 may contain up to 2 wt-% of suitable heat stabilizers and/or antioxidants including diphenylamines, amides, thioesters, phenolic antioxidants and phosphites. These stabilizers/antioxidants may be introduced directly or as a suitable heat stabilized concentrate during the manufacturing process and/or be melt mixed with the copolyetherester elastomer.

Thermoplastic Vulcanizate 1

Example E1

A vulcanizate blend containing about 48.1 wt-% of copolyetherester N° 1 based on the total weight of the vulcanizate blend. The rubber was an ethylene methyl-acrylate copolymer comprising 62 wt-% of methyl-acrylate, the weight percentage being based on the total weight of the copolymer. The rubber was crosslinked using about 3.3 wt-% of 2,5-dimethyl-2,5-di-(t-butylperoxy) hexyne-3 (DYBP) as peroxide curative and about 4.5 wt-% of organic multiolefinic co-agent diethylene glycol dimethacrylate (DEGDM), the weight percentage being based on the total weight of the rubber.

Thermoplastic Vulcanizate 2

Example E2

A vulcanizate blend containing about 50.2 wt-% of copolyetherester N° 2 based on the total weight of the vulcanizate blend. The rubber was an ethylene methyl-acrylate copolymer comprising 62 wt-% of methyl-acrylate, the weight percentage being based on the total weight of the copolymer. The rubber was crosslinked using about 2.7 wt-% of 2,5-dimethyl-2,5-di-(t-butylperoxy) hexyne-3 (DYBP) as peroxide curative and about 4.6 wt-% of organic multiolefinic co-agent diethylene glycol dimethacrylate (DEGDM) cure system (dynamic vulcanization), the weight percentage being based on the total weight of the rubber.

Thermoplastic Vulcanizate 3

Example E3

A vulcanizate blend containing about 32.5 wt-% of copolyetherester N° 3 based on the total weight of the vulcanizate blend. The rubber was an ethylene methyl-acrylate copolymer comprising 35 wt-% of methyl-acrylate, the weight percentage being based on the total weight of the copolymer. The rubber was crosslinked using about 1.3 wtt% of 2,5-dimethyl-2,5-di-(t-butylperoxy) hexane as peroxide curative and about 1.8 wtt% of organic multiolefinic co-agent diethylene glycol dimethacrylate (DEGDM) cure system (dynamic vulcanization), the weight percentage being based on the total weight of the rubber.

As required for the manufacturing process of thermoplastic vulcanizates and well-known to those skilled in the art, thermoplastic vulcanizate N° 1, N° 2 and N° 3 may contain up to 2 wt-% of suitable heat stabilizers and/or antioxidants including diphenylamines, amides, thioesters, phenolic antioxidants and phosphites. These stabilizers/antioxidants may be introduced directly or as a suitable heat stabilized concentrate during the manufacturing process and/or may be melt mixed with the thermoplastic vulcanizates. The thermoplastic vulcanizate may also contain up to 3 wt-% of a suitable color concentrate.

The thermoplastic vulcanizate according to the present invention (abbreviated as "E" in the Table) were prepared according to the process described in the detailed description and described in WO 2004/029155.

Compositions of the Examples and Comparative Examples (abbreviated as "C" in the Table) were melt-mixed blends; samples were prepared in a twin-screw extruder having barrel temperatures set at about 220° C. to about 240° C.

Measurements

The viscoelastic material properties, including the dynamic modulus and the tangent delta (tan δ) were measured using a Dynamic Mechanical Analyzer (DMA) (Metravib VA4000) in tensile vibration mode according to ISO 6721-4 non-resonance method. The tests were done on injection molded specimen having the dimensions given in Table 1. These samples were conditioned at 23° C. for at least 24 hours before the measurements. The tests were done at a standard frequency of 1 Hz and by continuously increasing the temperature from −100° C. to +200° C. at a heating rate of 2° C./min.

The melting temperature of the samples in the form of pellets was measured according to ISO 11357-3, DSC, 2$^{nd}$ heating cycle at 10° C./min heating and cooling rates and all experimental conditions given in the norm except for samples C1, E1, C2, E2 wherein holding time was 10 minutes at maximum temperature of 250° C. and one minute at minimum temperature of 40° C.

Results are given in Table 1.

etherester elastomer. As shown in Table 1, comparative copolyetherester elastomer (C2) presented a loss factor performance above 0.07 within a narrow temperature range (from −2 to +58° C.) and low temperature behavior is not ideal. In contrast, its vulcanizate derivative (E2) presented an elevated loss factor performance over the entire wide range of interest (−35° C. to +80° C.). In fact this vulcanizate derivative (E2) presented a sufficiently high loss factor (tan δ ≧0.07) over a significantly broad temperature range that extended even beyond the desired temperature range: −35° C. to +83° C. Furthermore, the copolyetherester vulcanizate E2 had an advantageous high melting point and thermal stability at 200° C. which is desirable for high performance demanding applications.

E3 was a vulcanizate blend of the comparative sample (C3) comprising a thermoplastic elastomer consisting of a copolyetherester elastomer. As shown in Table 1, comparative copolyetherester elastomer (C3) presented a reasonable loss factor (tan δ ≧0.07) only in a narrow range of temperature (from −60 to −7° C.) in comparison with the temperature range of interest (i.e. from −35° C. to +80° C.) and the range is shifted to lower temperatures, making it unsuitable for high temperature use. In contrast, its vulcanizate derivative (E3) presented an elevated loss factor performance over the entire wide range of interest (−35° C. to +80° C.). In fact this vulcanizate derivative (E3) presented a sufficiently high loss factor (tan δ ≧0.07) over a significantly broad temperature range that extended even beyond the desired temperature range: −57° C. to +200° C. Furthermore, the copolyetherester vulcanizate E3 had an advantageous high melting point and thermal stability at 200° C. which is desirable for high performance demanding applications. In addition to the fact that all the comparative samples (C1 to C3) did not have a suffi-

TABLE 1

| | Dimensions of the test specimen (mm) | $T_m$ (° C.) | $T_{(tan\delta)max}$ (° C.) // $tan\delta_{max}$ | Low T (° C.) (where tanδ ≧0.07) | High T (° C.) (where tanδ ≧0.07) | T range (° C.) (where tanδ ≧0.07) |
|---|---|---|---|---|---|---|
| C1 | 10 × 4.0 × 2.3 | 201 | −28 // 0.13 | −52 | +14 | 66 |
| E1 | 10 × 4.1 × 2.4 | 204 | −25 // 0.46 | −46 | +120 | 166 |
| C2 | 10 × 4.0 × 2.3 | 217 | +23 // 0.10 | −2 | +58 | 60 |
| E2 | 10 × 4.1 × 2.3 | 216 | −25 // 0.22 +25 / 0.12 | −35 | +83 | 118 |
| C3 | 20 × 4.0 × 2.2 | 208 | −47 // 0.29 | −60 | −7 | 53 |
| E3 | 10 × 4.3 × 1.2 | 210 | −47 // 0.10 −26 // 0.40 | −57 | 200 | 257 |

E1 was a vulcanizate blend of the comparative sample comprising a thermoplastic elastomer consisting of a copolyetherester elastomer (C1). As shown in Table 1, whereas the copolyetherester elastomer (C1) presented a reasonable loss factor (tan δ ≧0.07) only in a narrow range of temperature (from −52 to +14° C.) in comparison with the temperature range of interest (i.e. from −35° C. to +80° C.) and the range is shifted to lower temperatures, making it unsuitable for high temperature use. In contrast, its vulcanizate derivative (E1) presented an elevated loss factor performance over the entire wide range of interest (−35° C. to +80° C.). In fact this vulcanizate derivative (E1) presented a sufficiently high loss factor (tan δ ≧0.07) over a significantly broad temperature range that extended even beyond the desired temperature range: −46° C. to +120° C. Furthermore, the copolyetherester vulcanizate E1 had an advantageous high melting point and thermal stability at 200° C. which is desirable for high performance demanding applications.

E2 was a vulcanizate blend of the comparative sample (C2) comprising a thermoplastic elastomer consisting of a copolycient loss factor performance, i.e. tan δ values are not higher or equal to 0.07 along the whole temperature range of interest (i.e. from −35° C. to +80° C.), the use of the vulcanizate derivatives (E1 to E3) led not only to sufficient loss factor performance (tan δ ≧0.07) in this range but also to a at least two-fold increase of the temperature range over which the tan δ values are higher or equal to 0.07.

What is claimed is:

1. An article that reduces noise in use comprising a multilayer structure comprising:
   A. at least one polymeric layer comprising a thermoplastic vulcanizate composition comprising:
      (i) from about 15 to about 75 wt-% of at least one thermoplastic polyester or copolyetherester elastomer continuous phase; and
      (ii) from about 25 to about 85 wt-% of at least one poly(meth)acrylate or polyethylene/(meth)acrylate rubber that forms a dispersed phase, wherein the rubber is dynamically cross-linked with at least one peroxide free-radical initiator and at least one organic multiolefinic co-agent;

the weight percentage being based on the total weight of the thermoplastic vulcanizate composition (i+ii);

wherein the thermoplastic vulcanizate composition is characterized by having a tan δ, as determined according ISO 6721-4, non-resonance method, of greater than or equal to 0.07 within the ranqe of about −35° C. to about 80° C.; and B. at least one additional layer.

2. The article of claim 1, wherein the at least one additional layer is made from polymers others than thermoplastic vulcanizates, metals, glass, wood, fibers, fabrics, metal oxides, stone or concrete.

3. The article of claim 1, further comprising at least two additional layers comprising at least one metal selected from the group consisting of aluminum, aluminum alloys, copper, bronze, steel, stainless steel, chrome, titanium and mixtures of these and between which layers lie the at least one polymeric layer.

4. The article of claim 1, wherein the at least one polymeric layer has a thickness of at least about 10 μm and preferably between 25 and 500 μm.

5. A method for improving vibration damping performance or reducing noise generation in an appliance in which vibration damping and noise reduction is of concern, comprising:
   a) providing an article comprising a thermoplastic vulcanizate composition, the thermoplastic vulcanizate composition comprising:
      (i) from about 15 to about 75 wt-% of at least one thermoplastic polyester or copolyetherester elastomer continuous phase; and
      (ii) from about 25 to about 85 wt-% of at least one poly(meth)acrylate or polyethylene/(meth)acrylate rubber that forms a dispersed phase, wherein the rubber is dynamically cross-linked with at least one peroxide free-radical initiator and at least one organic multiolefinic co-agent;
   the weight percentage being based on the total weight of the thermoplastic vulcanizate composition (i+ii);
   wherein the thermoplastic vulcanizate composition is characterized by having a tan δ, as determined according ISO 6721-4, non-resonance method, of greater than or equal to 0.07 within the range of about −35° C. to about 80° C. and
   b) applying the article to an appliance, thereby forming a structure having efficient vibration damping and noise reduction characteristics over a temperature range of from at or about −35° C. to at or about 80° C.

6. The method of claim 5, wherein the at least one free-radical initiator comprised in the thermoplastic vulcanizate is one or more of 2,5-dimethyl-2,5-di-(t-butylperoxy)hexyne-3, t-butyl peroxybenzoate, 2,5-dimethyl-2,5-di-(t-butylperoxy)hexane, dicumyl peroxide, α,α-bis(t-butylperoxy)-2,5-dimethylhexane.

7. The method of claim 5, wherein the at least one organic multiolefinic co-agent comprised in thermoplastic vulcanizate is one or more of diethylene glycol diacrylate, ethylene glycol dimethacrylate, diethylene glycol dimethacrylate, N,N'-m-phenylene dimaleimide, triallylisocyanurate, trimethylolpropane trimethacrylate, tetraallyloxyethane, triallyl cyanurate, tetramethylene diacrylate, polyethylene glycol dimethacrylate.

8. The method of claim 5, wherein the copolyetherester elastomer is prepared from monomers comprising isophthalic acid, terephthalic acid and mixtures of these; 1,4-butanediol, 1,3-propanediol, and mixtures of these; and from monomers selected from the group consisting of poly(tetramethylene oxide) glycol, poly(trimethylene oxide) glycol and ethylene oxide-capped poly(propylene oxide) glycol.

9. The method of claim 5, wherein the thermoplastic vulcanizate composition further comprises one or more heat stabilizers and/or antioxidants.

10. The method of claim 5 wherein the appliance is a household appliance.

11. The method of claim 5 wherein the appliance is a structural component for machines.

12. The method of claim 5 wherein the appliance is a structural component for buildings.

13. The method of claim 5 wherein the appliance is a structural component for mechanical devices.

14. The method of claim 5 wherein the appliance is a structural component of a vehicle.

15. The method of claim 5 wherein the appliance is a noise-emitting component of an automobile.

* * * * *